Figure 1A:
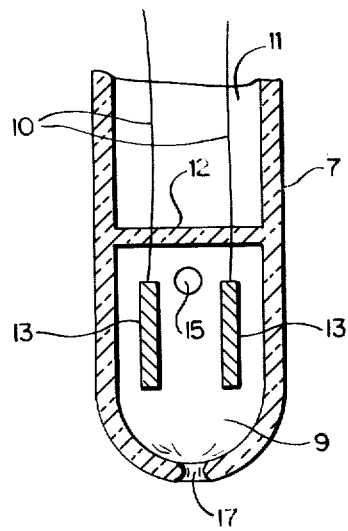

United States Patent [19]
Van Lenten et al.

[11] 3,939,401
[45] Feb. 17, 1976

[54] CONDUCTIVITY CELL ELECTRODE ENCLOSURE

[75] Inventors: Constance Van Lenten, Hawthorne; Robert Rosenthal, Tenafly; Elmer A. Sperry, III, Pompton Plains, all of N.J.

[73] Assignee: Beckman Instruments, Inc., Fullerton, Calif.

[22] Filed: June 2, 1972

[21] Appl. No.: 259,347

Related U.S. Application Data

[63] Continuation of Ser. No. 50,278, June 26, 1970, abandoned.

[52] U.S. Cl............................................ 324/30 B
[51] Int. Cl.²....................................... G01N 27/28
[58] Field of Search........ 324/30 R, 30 B, 29, 29.5, 324/61 P, 65 P

[56] References Cited
UNITED STATES PATENTS

| | | | |
|---|---|---|---|
| 1,518,211 | 12/1924 | Maue | 324/30 B |
| 1,592,979 | 7/1926 | Keeler | 324/30 B |
| 1,951,035 | 3/1934 | Parker | 324/30 B |
| 2,789,887 | 4/1957 | Cruikshank | 324/30 B |
| 3,028,546 | 4/1962 | Sproule | 324/30 B |
| 3,265,962 | 8/1966 | Otto | 324/30 B |

*Primary Examiner*—Robert J. Corcoran
*Attorney, Agent, or Firm*—R. J. Steinmeyer; P. R. Harder

[57] ABSTRACT

An electrode housing for a fluid conductivity cell contains a chamber in which electrodes are securely positioned, the walls of the housing being electrically nonconducting and having at least one chamber duct penetrating the walls of the housing for the ingress and egress of fluid to be measured. The chamber duct is located relative to the electrodes such that it is substantially coincident with at least a portion of a line of equipotential established at the inside surface of the chamber in response to a voltage applied to the electrodes. The chamber duct is a size and shape to provide a negligible voltage drop across any dimension thereby substantially confining a conduction of current between the electrodes to the chamber of the electrode housing.

10 Claims, 7 Drawing Figures

U.S. Patent  Feb. 17, 1976  3,939,401

INVENTORS
CONSTANCE VAN LENTEN
ROBERT ROSENTHAL
ELMER A. SPERRY, III

BY *Paul K. Harder*
ATTORNEY

CONDUCTIVITY CELL ELECTRODE ENCLOSURE

This application is a continuation of copending prior application Ser. No. 50,278 filed June 26, 1970, which has become abandonded.

The present invention relates to conductivity cells and more particularly to conductivity cell enclosures for confining current conduction to the interior of the enclosure.

In the field of fluid conductivity measurement, it has been the general practice to employ a pair of electrodes which are inserted in the fluid to be measured to perform the conductivity measurement. An electrical bias is applied to the electrodes resulting in an electric field being established in the fluid between the electrodes. This electric field causes the ions in the solution to migrate toward one of the electrodes depending upon the polarity of the electrode and the polarity of the ion thereby establishing a current in the fluid. Although such devices have served the purpose, they have not proved entirely satisfactory under all conditions of service for the reason that considerable difficulty has been experienced in that the current between the electrodes is affected by the proximity of objects and surfaces near the electrodes. These objects and surfaces intercept the electric field and prevent the flow of current between the electrodes in the region of the objects and surfaces thereby altering the measurement of conductivity. Although the electrodes are generally held in a cell-like structure, the openings into the cell have either been of such dimensions as to permit current conductivity exterior to the cell or the openings have been asymmetrically located resulting in the conduction of current out of one opening and into another exterior to the cell.

Heretofore dip-type conductivity cells, which are inserted into the fluids to be measured, with cell constants greater than about 0.3/cm were designed in such a way that some of the current conducted from one electrode to the other passed through the electrolyte surrounding and exterior to the conductivity cell. This type of conduction resulted because the electrodes were spaced apart and located asymmetrically to the cell openings. Therefore the cell was sensitive to the proximity of external objects and surfaces. If such a cell is brought too close to the bottom of a nonconducting container, some of the external current will be blocked by the surface of the container and the conductivity of the solution will appear lower than that measurement obtained by an unobstructed measurement. Conversely, if the cell were to be brought too close to an electrical conductor such as a piece of metal, the external current path would be lower in resistance, and the apparent conductivity as measured under these circumstances would be greater than the true value.

Those concerned with the development of conductivity cells have long recognized the need for electrode enclosures which permit conductivity measurements insensitive to the proximity of external objects and surfaces. The present invention fulfills this need.

The general purpose of this invention is to provide a conductivity cell which embraces all the advantages of similarly employed conductivity measurement cells and possesses none of the aforedescribed disadvantages. To attain this, the present invention contemplates a unique electrode enclosure having openings into the enclosure of a size and shape and specifically located with respect to the electrodes whereby current conduction external to the enclosure is avoided.

An object of the present invention is the provision of an electrode enclosure for conductivity cells in which the conduction of current is confined to the interior of the enclosure.

Another object is to provide a conductivity cell which has cell openings located in such a way that no electrical current will flow externally between the openings.

A further object of the invention is the provision of an electrode enclosure for a conductivity cell which has openings therein for the ingress and egress of fluids to be measured which openings are located with respect to the electrodes at equipotential points thereby preventing the conduction of electrical current from opening to opening exterior to the enclosure.

Still another object is to provide a conductivity cell for the measurement of conductivity of fluids which is entirely independent of its position relative to external conducting and nonconducting surfaces and objects.

Yet another object of the present invention is the provision of a conductivity cell electrode enclosure having a multiplicity of openings therein for the ingress and egress of fluids to be measured which openings are located with respect to the electrodes at equipotential points such that no electrical current will flow external to the enclosure from opening to opening and which openings are sufficiently small that the fluid will be held within the electrode enclosure by the surface tension of the fluid at the openings thereby enabling the conductivity cell electrode enclosure to be removed entirely from the fluid without changing the conductivity measurement reading thereby isolating interference from the measurement that may be caused by such factors as temperature, cavitation caused by ultrasonic agitation in the fluid, gas bubbles, electrical currents, and other electrical paths which may be present in the main body of the fluid.

Figure 1B:
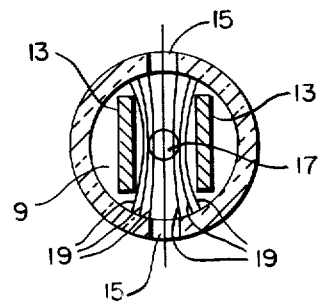
Figure 2A:
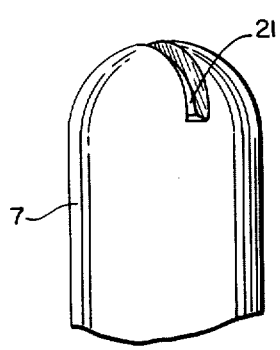
Figure 2B:
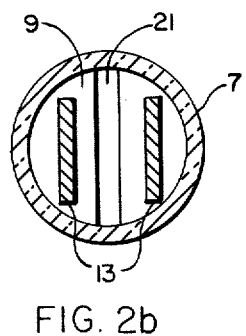
Figure 3:
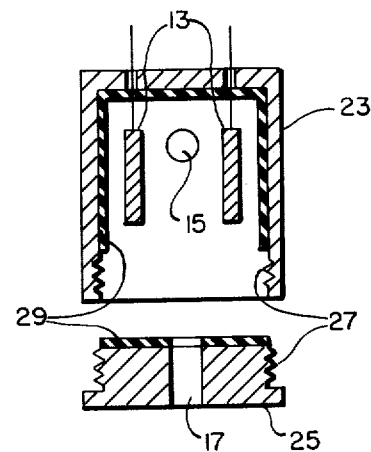
Figure 4B:
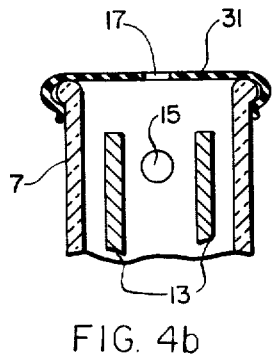
Figure 4A:
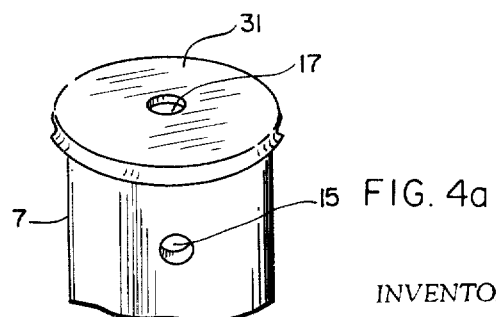

Other objects and many of the attendant advantages of this invention will be readily appreciated as the same becomes better understood by reference to the following detailed description when considered in connection with the accompanying drawing in which like reference numerals designate like parts throughout the figures thereof and wherein:

FIGS. 1(a) and 1(b) illustrate orthogonal cross-sectional views of a conductivity cell electrode enclosure embodiment in accord with the teachings of the present invention;

FIGS. 2(a) and 2(b) illustrate a pictorial view and a cross-sectional view of another embodiment of the conductivity cell electrode enclosure;

FIG. 3 illustrates a cup electrode enclosure with an interchangeable threaded screw-on top; and FIGS. 4(a) and 4(b) show a pictorial and a cross-sectional view of another embodiment of the present invention having an interchangeable snap-on top.

Turning now to FIG. 1(a), a body member 7, which may be in the form of a cylinder or a section of tubing having any desirable cross-sectional shape, is divided into a lower chamber 9 and an upper chamber 11 by a thin walled member 12. Body member 7 may be composed of an electrical insulating material such as glass, plastic or other materials having similar characteristics. It will also become apparent that body member 7 may be formed from a conducting material provided that the interior of chamber 9 is coated with an electrical insulating material such as that described above.

The walls of chamber 9 are penetrated by a chamber duct or opening 17, which may be formed by tapering the walls of a glass cylinder into an opening of desired size, and a pair of oppositely disposed chamber ducts or openings 15 of which only one appears in FIG. 1(a). Conductivity electrodes 13 are securely positioned within chamber 9 by conducting supports 10 which penetrate through thin walled member 12 into chamber 11.

FIG. 1(b) illustrates the relative positions of electrodes 13, holes 15 and opening 17. The lines 19 show the position of lines of equipotential established when an electrical bias is applied between electrodes 13. Opening 17 and the pair of oppositely disposed openings 15 are located to be coincident with at least a portion of a line of equipotential established at the inside surface of chamber 9. Although only a pair of openings 15 are illustrated, a multiplicity of small holes located along the line of equipotential may be employed.

Another embodiment of the present invention is illustrated in FIG. 2(a). Body member 7 is illustrated having a slot 21 penetrating the walls of chamber 9 instead of holes 15 and 17.

FIG. 2(b) illustrates the relative position of slot 21 and pair of electrodes 13. Slot 21 is located to coincide with a line of equipotential established at the inside surface of chamber 9 as discussed above in connection with FIG. 1(b).

The cross-sectional view of FIG. 3 illustrates an embodiment of the present invention where body member 23 is in the shape of a cup having a screw top 25 and mating threads 27 by which top 25 and body 23 may be screwed together. Body member 23 may be composed of an electrical conducting material such as stainless steel or other chemically inert electrical conductors, which is coated on the inside by an electrical insulation 29. Top cover 25 also is coated with insulation 29 such that when the top is assembled with the body 23, the interior surface of the enclosure is entirely covered with electrical insulation. Body 23 is penetrated by a pair of oppositely disposed holes 15 of which one is shown. Cover 25 contains opening 17 the size of which may be varied by interchanging with other covers having different sized openings.

There is illustrated in FIG. 4(a) a pictorial view of body member 7 having a snap-on cover 31 in which opening 17 is located.

FIG. 4(b) further illustrates in a cross-sectional view the relative position of electrodes 13 and openings 15 and 17 with snap-on cover 31 affixed to body member 7. The openings again must fall on a line of equipotential established at the inside surface of the enclosure by a voltage applied between the electrodes. Snap-on cover 31 with opening 17 may be easily removed and replaced by another cover having a different sized opening 17.

Turning now to FIGS. 1(a) and 1(b), body member 7 with chamber 9 and openings 15 and 17 function to confine current conduction between electrodes 13 to the interior of chamber 9. Openings 17 and 15 allow the fluid being measured to enter into chamber 9 and surround the electrodes 13. The size of the openings 15 and 17 can be made sufficiently small that when the electrode enclosure is removed from the fluid, the fluid is retained in chamber 9 by the surface tension across openings 15 and 17. As shown in the drawing the openings or apertures 15 and 17 are relatively small in diameter or in width in comparison with the spacing between the electrodes 13, and there is appreciable spacing between the outer edges of the apertures 15 and 17 and projections of the inner surfaces of the electrodes 13. In FIG. 2 the narrow dimension or the width is the dimension transverse to the planar electrodes 13 and to the lines of equipotential 19. Where surface tension is used to confine the fluid to chamber 9, the fluid can be made to enter or to leave the chamber by rapidly shaking the electrode enclosure in the fluid and out of the fluid respectively. As will be understood by those skilled in the art, the surface tension of a fluid determines the maximum diameter of a circular opening or the width of a rectangular opening across which a surface film of sufficient strength will be formed to retain the fluid in the aperture and overcome the pressure to which the film is subjected by the fluid column above the aperture.

Since openings 15 and 17 are located along a line of equipotential between electrodes 13, there is substantially no conduction of current exterior to body member 7, all of the openings being essentially at the same potential. Therefore, exterior objects or surfaces do not affect the conductivity measurement being made interior to body member 7 and confined to chamber 9.

Turning to FIGS. 2(a) and 2(b), an opening such as slot 21 can satisfy the requirement of no conduction exterior to body member 7, if such a slot lies along a line of equipotential between the electrodes 13. Since there is no voltage difference along the slot, there will be substantially no electric field external to body member 7 and hence no current conduction. By making the narrow dimension of slot 21 sufficiently small, surface tension of the fluid can be made to retain the fluid in chamber 9 when the electrode enclosure is removed from the fluid being measured similar to the surface tension employed with respect to openings 15 and 17 discussed in connection with FIGS. 1(a) and 1(b). Fluid again can be made to enter and exit from chamber 9 by rapidly shaking the electrode enclosure as already discussed.

Depending upon the viscosities of the fluids being measured, it may be desirable from time to time to change the size of at least one of the openings into the electrode enclosure. Since openings 15 into the enclosure may be considered vent openings, it may be sufficient from most applications to change the size of opening 17 alone. As illustrated in FIG. 4, this may be performed by providing the electrode enclosure with a screw-on cover such as cover 25. Another way to accomplish the changing of opening 17 is by snap-on cover 31 illustrated in FIG. 5. Cover 31 is readily removed and replaced by snapping it on and off from body member 7.

It now should be apparent that the present invention provides a conductivity cell electrode enclosure which is unaffected by its exterior environment and which retains fluid in its interior even when removed from the fluid being measured providing a conductivity measurement which is isolated from interferences in the main body of the fluid being measured. Although particular components, structure and form have been discussed in connection with a specific embodiment of an electrode enclosure constructed in accordance with the teachings of the present invention, others may be utilized. Furthermore, it will be understood that although an exemplary embodiment of the present invention has been disclosed and discussed, other applications and circuit arrangements are possible and that the embodiments disclosed may be subjected to various changes, modifications and substitutions without necessarily departing from the invention.

What is claimed is:

1. A cell for measuring the conductivity of fluids having two parallel planar electrodes mounted interior to the cell comprising; a section of glass tubing separated into first and second volumes by an interior glass divider, said first volume having two vent holes oppositely disposed and symmetrically located in the walls of said first volume, the end of said section of glass tubing associated with said first volume being tapered to form a third vent hole, the electrodes being mounted within said first volume such that all three vent holes are bisected by a plane of equipotential formed in response to a voltage potential applied to the planar electrodes thereby substantially confining conduction of current to the interior of said first volume.

2. An electrode enclosure for a fluid conductivity cell in which a current is passed between electrodes proportional to the conductivity of fluid introduced into the enclosure comprising a housing having a chamber, a pair of electrodes securely positioned in said chamber with a predetermined spacing, said chamber having electrically nonconductive walls having at least one aperture formed in a wall of said chamber for the ingress and egress of fluid, with said aperture in the chamber being located relative to said electrodes to be substantially coincident with at least a portion of a line of equipotential established at the inside surface of said chamber when a voltage is applied to the electrode and said aperture having a dimension measured transverse to such line of equipotential, which dimension is small in comparison with the electrode spacing to provide a negligible voltage drop across any dimension of said aperture, thereby substantially confining the conduction of current to the chamber of said housing.

3. The electrode enclosure of claim 2 wherein one aperture is formed as a rectangular slot having the longest dimension along said line of equipotential.

4. The electrode enclosure of claim 2 wherein a multiplicity of small holes are formed in said walls, aligned along said line of equipotential.

5. A conductivity cell for current measurement in a fluid having a given surface tension, the cell comprising:
a pair of electrodes spaced from each other having lines of equipotential between them when voltage is applied thereto;
means connected to said electrodes for providing mechanical support and electrical conduction thereto;
an enclosure having electrically nonconducting walls penetrated by and secured to the means to support and conduct, said enclosure having at least one aperture formed therein located symmetrically with respect to each of said pair of electrodes to confine to the interior of said enclosure the conduction of current between said electrodes in response to a voltage potential impressed upon said means to support and conduct, with said aperture having a width less than the width of film capable of supporting the column of fluid determined by the dimensions of the enclosure for a fluid of such surface tension, thereby containing fluid in said enclosure by surface tension of said fluid across said aperture.

6. The conductivity cell defined in claim 5 wherein said enclosure is a cylinder of glass having one end tapered to a rounded surface, the interior of the cylinder being separated into two volumes by a glass divider through which said means to support and conduct is mounted to support said electrodes in the volume defined by said one end and said divider.

7. The conductivity cell defined in claim 5 wherein said enclosure comprises:
a cup having cylindrical side walls and a base at one end and an opening at the other end, the base being penetrated by and secured to said means for supporting and conducting; and
a cup cover including at least one aperture formed therein, said aperture being symmetrically located on said cover with respect to said electrodes, said cover being removably attached to the opening of said cup.

8. The conductivity cell defined in claim 5 wherein the electrodes have inner surfaces lying along parallel planes and the apertures are spaced from the projections of the inner surfaces of the electrodes and small in area in comparison with the area of the electrode inner surfaces.

9. An electrode enclosure for a fluid conductive cell for measuring conductivity of a fluid having a given surface tension, in which enclosure a current is passed between electrodes proportional to the conductivity of fluid introduced into the enclosure, comprising
a housing having a chamber,
a pair of spaced electrodes positioned in said chamber, said chamber having electrically nonconducting walls and having at least one aperture formed in a wall of said chamber for the ingress and egress of fluid, with said aperture in a wall being located relative to said electrodes to be substantially coincident with at least a portion of a line of equipotential established at the inside surface of said chamber when a voltage is applied to the electrodes, to provide a negligible voltage drop across any dimension of said aperture and the width of said aperture measured transverse to such lines of equipotential is no greater than the width of a surface film capable of supporting fluid of such surface tension in said aperture, thereby substantially confining the conduction of current to the chamber of said housing and containing the fluid in said chamber.

10. A conductivity cell for current measurement in a fluid having a given surface tension, the cell comprising:
a pair of electrodes;
means connected to said electrodes for providing mechanical support and electrical conduction thereto;
an enclosure having electrically nonconducting walls penetrated by and secured to the means to support and conduct, said enclosure surrounding said electrodes and having at least one aperture formed therein located symmetrically with respect to each of said pair of electrodes to confine to the interior of said enclosure the conduction of current between said electrodes in response to a voltage potential impressed on said means to support and conduct, with said aperture sufficiently narrow to contain fluid in said enclosure by surface tension of said fluid across said aperture.

* * * * *